United States Patent
Kath et al.

(10) Patent No.: US 6,844,349 B2
(45) Date of Patent: Jan. 18, 2005

(54) SALT FORMS OF E-2-METHOXY-N-(3-{4-[3 METHYL-4-(6-METHYL-PYRIDIN-3-YLOXY)-PHENYLAMINO]-QUINAZOLIN-6-YL}-ALLYL)-ACETAMIDE AND METHOD OF PRODUCTION

(75) Inventors: John C. Kath, Waterford, CT (US); Daniel T. Richter, Groton, CT (US); Zheng J. Li, Quaker Hill, CT (US); Andrew V. Trask, Stonington, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/315,862

(22) Filed: Dec. 10, 2002

(65) Prior Publication Data

US 2003/0158217 A1 Aug. 21, 2003

Related U.S. Application Data

(60) Provisional application No. 60/340,885, filed on Dec. 12, 2001.

(51) Int. Cl.$^7$ .................. C07D 239/94; A61K 31/517; A61P 35/00
(52) U.S. Cl. .................. 514/266.21; 544/284
(58) Field of Search ...................... 514/266.21; 544/284

(56) References Cited

U.S. PATENT DOCUMENTS 6,123,939 A   9/2000   Shawver ................. 424/130.1

FOREIGN PATENT DOCUMENTS

| WO | 9609294 | 3/1996 |
| WO | 9730034 | 8/1997 |
| WO | 9802434 | 1/1998 |
| WO | 0198277 | 12/2001 |

OTHER PUBLICATIONS

Garratt AN, Ozcelik C, Birchmeier C. Trends Cardiovasc Med. Feb. 2003;13(2):80–6. Medline abstract PMID: 12586444.*
Mendelsohn, J. et al, Oncogene (2000), 19, 6550–6565.*
Stern, D.F., Breast Cancer Res., 2000, 2, 176–183.*
Denny, W.A., Farmaco, 2001, 56(1–2), 51–56, Medline abstract PMID 11347967.*
Holbro, T. et al, Exp. Cell Res., 2003, 284(1), 99–110, Medline abstract PMID 12648469.*
Slichenmeyer,W.J. et al, Semin. Oncol., 2001 5(Suppl 16) 67–79., Medline abstract PMID 11706398.*
International Search Report for PCT/IB02/04708 issued Nov. 11, 2002 (5 pages).
R. Roskoski, *BBRC*, vol. 319 (2004): 1–11 "The ErbB/HER receptor protein–tyrosine kinases and cancer".
Letrent, "Pure Her2 Inhibition with a Small Molecule", 4$^{th}$ International Symposium on Translational Research in Oncology, Jul. 15–18, 2004, Dublin, Ireland.

* cited by examiner

*Primary Examiner*—Thomas C. McKenzie
(74) *Attorney, Agent, or Firm*—Peter C. Richardson; Pamela C. Ancona; Garth Butterfield

(57) ABSTRACT

The invention relates to succinate and malonate complexes of E-2-Methoxy-N-(3-{4-[3-methyl-4-(6-methyl-pyridin-3-yloxy)-phenylamino]-quinazolin-6-yl}-allyl)-acetamide having the following formula I:

formula I

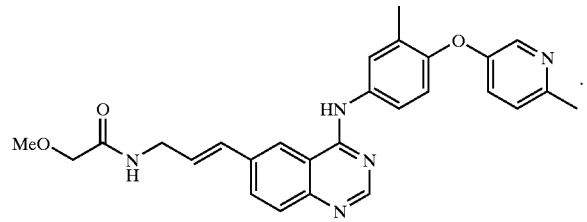

More particular the present invention relates to monosuccinate, hemisuccinate, sesquisuccinate and di-malonate complexes of formula I. The invention also relates to pharmaceutical compositions containing the succinate and malonate complexes of formula I. The invention further relates to methods of treating hyperproliferative diseases, such as cancers, in mammals, especially humans by administering the above complexes and to methods of preparing the above complexes.

30 Claims, No Drawings

SALT FORMS OF E-2-METHOXY-N-(3-{4-[3 METHYL-4-(6-METHYL-PYRIDIN-3-YLOXY)-PHENYLAMINO]-QUINAZOLIN-6-YL}-ALLYL)-ACETAMIDE AND METHOD OF PRODUCTION

CONTINUING APPLICATION DATA

This invention claims the benefit of U.S. Provisional Application Ser. No. 60/340,885, filed Dec. 12, 2001, the contents of the aforementioned patent applications are hereby incorporated by reference in their entirety.

BACKGROUND OF THE INVENTION

This invention relates to complexes of E-2-Methoxy-N-(3-{4-[3-methyl-4-(6-methyl-pyridin-3-yloxy)-phenylamino]-quinazolin-6-yl}-allyl)-acetamide having the formula I:

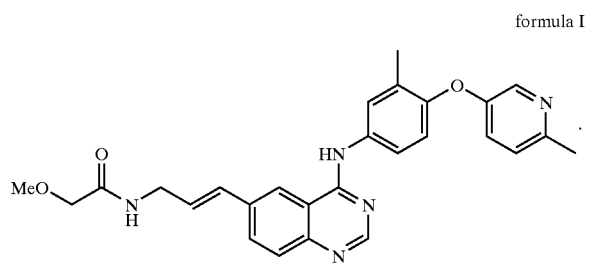

formula I

Formula I in its free base form is described in co-pending U.S. Ser. No. 09/883,752, filed Jun. 18, 2001, the disclosure of which is hereby incorporated herein by reference in its entirety. The foregoing application is assigned in common with the present application. The free base of formula I is useful in the treatment of hyperproliferative diseases, such as cancers.

The present invention provides for succinate and malonate complexes of E-2-Methoxy-N-(3-{4-[3-methyl-4-(6-methyl-pyridin-3-yloxy)-phenylamino]-quinazolin-6-yl}-allyl)-acetamide.

The present invention also provides for the monosuccinate, hemisuccinate, sesquisuccinate and di-malonate complexes of E-2-Methoxy-N-(3-{4-[3-methyl-4-(6-methyl-pyridin-3-yloxy)-phenylamino]-quinazolin-6-yl}-allyl)-acetamide.

The present invention further relates to methods of making the monosuccinate, hemisuccinate, sesquisuccinate and di-malonate complexes of E-2-Methoxy-N-(3-{4-[3-methyl-4-(6-methyl-pyridin-3-yloxy)-phenylamino]-quinazolin-6-yl}-allyl)-acetamide. hemisuccinate, sesquisuccinate and di-malonate complexes of E-2-Methoxy-N-(3-{4-[3-methyl-4-(6-methyl-pyridin-3-yloxy)-phenylamino]-quinazolin-6-yl}-allyl)-acetamide. The invention also The present invention further relates to methods of making the monosuccinate, relates to pharmaceutical compositions containing the monosuccinate, hemisuccinate, sesquisuccinate and di-malonate complexes of the compound of formula I. The complexes of the present invention are useful in the treatment of hyperproliferative diseases, such as cancers, in mammals, especially humans. The invention also relates to methods of administering the complexes of formula I to treat hyperproliferative diseases.

SUMMARY OF THE INVENTION

The present invention relates to succinate and malonate complexes of E-2-Methoxy-N-(3-{4-[3-methyl-4-(6-methyl-pyridin-3-yloxy)-phenylamino]-quinazolin-6-yl}-allyl)-acetamide having the following formula I:

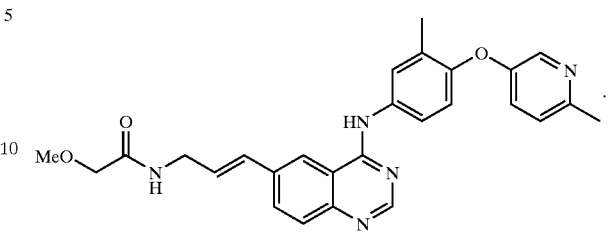

formula I

In one preferred embodiment the invention relates to monosuccinate, hemisuccinate, sesquisuccinate and di-malonate complexes of E-2-Methoxy-N-(3-{4-[3-methyl-4-(6-methyl-pyridin-3-yloxy)-phenylamino]-quinazolin-6-yl}-allyl)-acetamide.

In a preferred embodiment the invention relates to a monosuccinate complex of E-2-Methoxy-N-(3-{4-[3-methyl-4-(6-methyl-pyridin-3-yloxy)-phenylamino]-quinazolin-6-yl}-allyl)-acetamide.

In another preferred embodiment the invention relates to a hemisuccinate complex of E-2-Methoxy-N-(3-{4-[3-methyl-4-(6-methyl-pyridin-3-yloxy)-phenylamino]-quinazolin-6-yl-}-allyl)-acetamide.

In a more preferred embodiment the invention relates to a sesquisuccinate complex of E-2-Methoxy-N-(3-{4-[3-methyl-4-(6-methyl-pyridin-3-yloxy)-phenylamino]-quinazolin-6-yl}-allyl)-acetamide.

In a another more preferred embodiment the invention relates to a di-malonate complex of E-2-Methoxy-N-(3-{4-[3-methyl-4-(6-methyl-pyridin-3-yloxy)-phenylamino]-quinazolin-6-yl}-allyl)-acetamide.

The present invention is also directed to processes for preparing the monosuccinate, hemisuccinate, sesquisuccinate and di-malonate complexes of E-2-Methoxy-N-(3-{4-[3-methyl-4-(6-methyl-pyridin-3-yloxy)-phenylamino]-quinazolin-6-yl}-allyl)-acetamide comprising combining the free base with one of the aforementioned complexes in the presence of a suitable organic solvent.

The sesquisuccinate and di-malonate complexes of E-2-Methoxy-N-(3-{4-[3-methyl-4-(6-methyl-pyridin-3-yloxy)-phenylamino]-quinazolin-6-yl}-allyl)-acetamide have been characterized by elemental analysis.

It has unexpectedly been found that the sesquisuccinate and di-malonate complexes of E-2-Methoxy-N-(3-{4-[3-methyl-4-(6-methyl-pyridin-3-yloxy)-phenylamino]-quinazolin-6-yl}-allyl)-acetamide have high crystallinity, i.e., substantially free of amorphous material. Such complexes have the advantage that they provide more reproducible dosing results. The sesquisuccinate and di-malonate complexes of E-2-Methoxy-N-(3-{4-[3-methyl-4-(6-methyl-pyridin-3-yloxy)-phenylamino]-quinazolin-6-yl}-allyl)-acetamide are substantially hygroscopically stable, which alleviates potential problems associated with weight changes of the active ingredient during the manufacture of capsules or tablets.

The present invention also relates to a method for the treatment of abnormal cell growth in a mammal which comprises administering to said mammal an amount of succinate or malonate complex of E-2-Methoxy-N-(3-{4-[3-methyl-4-(6-methyl-pyridin-3-yloxy)-phenylamino]-quinazolin-6-yl}-allyl)-acetamide, that is effective in treating abnormal cell growth. In one preferred embodiment, the invention relates to method for the treatment of abnormal cell growth in a mammal which comprises administering to said mammal an amount of monosuccinate, hemisuccinate, sesquisuccinate or di-malonate complex of E-2-Methoxy-N-(3-{4-[3-methyl-4-(6-methyl-pyridin-3-yloxy)-phenylamino]-quinazolin-6-yl}-allyl)-acetamide, that is effective in treating abnormal cell growth.

In one embodiment the abnormal cell growth treated is cancer.

In one embodiment of the present the cancer is selected is selected from lung cancer, non small cell lung (NSCL) cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), colorectal cancer (CRC), primary CNS lymphoma, spinal axis tumors, brain stem glioma, pituitary adenoma, or a combination of one or more of the foregoing cancers.

In a preferred embodiment of the present invention, cancer is selected from breast cancer, colon cancer, ovarian cancer, non small cell lung (NSCL) cancer, colorectal cancer (CRC), prostate cancer, bladder cancer, renal cancer, gastric cancer, endometrial cancer, head and neck cancer, and esophagel cancer.

In a more preferred embodiment of the present invention, the cancer is selected from renal cell carcinoma, gastric cancer, colon cancer, breast cancer, and ovarian cancer.

In a more preferred embodiment, the said cancer is selected from colon cancer, breast cancer or ovarian cancer.

Another embodiment of the present invention relates to method for the treatment of abnormal cell growth in a mammal which comprises administering to said mammal an amount of succinate or malonate complex of E-2-Methoxy-N-(3-{4-[3-methyl-4-(6-methyl-pyridin-3-yloxy)-phenylamino]-quinazolin-6-yl}-allyl)-acetamide, that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

Another embodiment of the present invention relates to method for the treatment of abnormal cell growth in a mammal which comprises administering to said mammal an amount of monosuccinate, hemisuccinate, sesquisuccinate or di-malonate complex of E-2-Methoxy-N-(3-{4-[3-methyl-4-(6-methyl-pyridin-3-yloxy)-phenylamino]-quinazolin-6-yl}-allyl)-acetamide, that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

Another embodiment of the present invention relates to a method for the treatment of abnormal cell growth in a mammal which comprises administering to said mammal an amount of succinate or malonate complex of E-2-Methoxy-N-(3-{4-[3-methyl-4-(6-methyl-pyridin-3-yloxy)-phenylamino]-quinazolin-6-yl}-allyl)-acetamide, that is effective in treating abnormal cell growth in combination in combination with a cytotoxic.

In one preferred embodiment of the present invention the cytotoxic is Taxol® (paclitaxel).

The present invention further relates to a method for the treatment of abnormal cell growth in a mammal which comprises administering to said mammal an amount of a succinate or malonate complex of formula 1 that is effective in treating abnormal cell growth in combination with a compound selected from the group consisting of Cyclophosphamide, 5-Fluorouracil, Floxuridine, Gemcitabine, Vinblastine, Vincristine, Daunorubicin, Doxorubicin, Epirubicin, Tamoxifen, Methylprednisolone, Cisplatin, Carboplatin, CPT-11, gemcitabine, paclitaxel, and docetaxel.

In one preferred embodiment, the invention relates to a method for the treatment of abnormal cell growth in a mammal which comprises administering to said mammal an amount of a succinate or malonate complex of formula 1 that is effective in treating abnormal cell growth in combination with a compound selected from the group consisting Tamoxifen, Cisplatin, Carboplatin, paclitaxel and docetaxel.

A preferred embodiment invention relates to a method for the treatment of abnormal cell growth in a mammal which comprises administering to said mammal an amount of monosuccinate, hemisuccinate, sesquisuccinate or di-malonate complex of E-2-Methoxy-N-(3-{4-[3-methyl-4-(6-methyl-pyridin-3-yloxy)-phenylamino]-quinazolin-6-yl}-allyl)-acetamide, that is effective in treating abnormal cell growth in combination in combination with a cytotoxic.

In one preferred embodiment of the present invention the cytotoxic is Taxol® (paclitaxel).

The present invention further relates to a method for the treatment of abnormal cell growth in a mammal which comprises administering to said mammal an amount of a sesquisuccinate or di-malonate complex of formula 1 that is effective in treating abnormal cell growth in combination with a compound selected from the group consisting of Cyclophosphamide, 5-Fluorouracil, Floxuridine, Gemcitabine, Vinblastine, Vincristine, Daunorubicin, Doxorubicin, Epirubicin, Tamoxifen, Methylprednisolone, Cisplatin, Carboplatin, CPT-11, gemcitabine, paclitaxel, and docetaxel.

In one preferred embodiment, the invention relates to a method for the treatment of abnormal cell growth in a mammal which comprises administering to said mammal an amount of a sesquisuccinate or di-malonate complex of formula 1 that is effective in treating abnormal cell growth in combination with a compound selected from the group consisting Tamoxifen, Cisplatin, Carboplatin, paclitaxel and docetaxel.

The invention further relates to a pharmaceutical composition for the treatment of abnormal cell growth in a mammal comprising an amount of a succinate or malonate complex of formula 1, that is effective in treating abnormal cell growth, and a pharmaceutically acceptable carrier.

The invention further relates to a pharmaceutical composition for the treatment of abnormal cell growth in a mammal comprising an amount of a monosuccinate, hemisuccinate, sesquisuccinate or di-malonate complex of formula 1, that is effective in treating abnormal cell growth, and a pharmaceutically acceptable carrier.

This invention also relates to a method for the treatment of abnormal cell growth in a mammal, including a human, comprising administering to said mammal an amount of a monosuccinate, hemisuccinate, sesquisuccinate or di-malonate complex of formula 1, or a solvate or prodrug thereof, that is effective in treating abnormal cell growth. In one embodiment of this method, the abnormal cell growth is cancer, including, but not limited to, lung cancer, non small cell lung (NSCL) cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), colorectal cancer (CRC), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal, including a human, which comprises administering to said mammal a monosuccinate, hemisuccinate, sesquisuccinate or di-malonate complex of formula 1, or a solvate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a monosuccinate, hemisuccinate, sesquisuccinate or di-malonate complex of formula 1, or a solvate or prodrug thereof, that is effective in treating abnormal cell growth, and a pharmaceutically acceptable carrier. In one embodiment of said composition, said abnormal cell growth is cancer, including, but not limited to, lung cancer, non small cell lung (NSCL) cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), colorectal cancer (CRC), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

The invention also relates to a pharmaceutical composition for the treatment of abnormal cell growth in a mammal, including a human, which comprises a succinate or malonate complex of formula 1 or a solvate or prodrug thereof, that is effective in treating abnormal cell growth in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a pharmaceutical composition for the treatment of abnormal cell growth in a mammal, including a human, which comprises a monosuccinate, hemisuccinate, sesquisuccinate or di-malonate complex of formula 1 or a solvate or prodrug thereof, that is effective in treating abnormal cell growth in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method for treating a mammal having cancer characterized by an overexpression of erbB2, comprising administering to the mammal a succinate or malonate complex of formula 1 in an amount that is effective in treating said cancer characterized by the overexpression of erbB2.

A preferred embodiment of the present invention relates to a relates to a method for treating a mammal having cancer characterized by an overexpression of erbB2, comprising administering to the mammal a monosuccinate, hemisuccinate, sesquisuccinate or di-malonate complex of formula 1 in an amount that is effective in treating said cancer characterized by the overexpression of erbB2.

The invention also relates to a method for treating a mammal having a disease characterized by an overexpression of erbB2, comprising administering to the mammal a succinate or malonate complex of formula 1 in an amount that is effective in treating a disease characterized by the overexpression of erbB2.

A preferred embodiment of the present invention relates to a method for treating a mammal having a disease characterized by an overexpression of erbB2, comprising administering to the mammal a monosuccinate, hemisuccinate, sesquisuccinate or di-malonate complex of formula 1 in an amount that is effective in treating a disease characterized by the overexpression of erbB2.

The invention also relates to a method inducing cell death comprising exposing a cell which overexpresses erbB2 to an effective amount of a succinate or malonate complex of formula 1. In one embodiment the cell is a cancer cell in a mammal, preferably a human.

A preferred embodiment of the present invention relates to a method of inducing cell death comprising exposing a cell which overexpresses erbB2 to an effective amount of a monosuccinate, hemisuccinate, sesquisuccinate or di-malonate complex of formula 1. In one embodiment the cell is a cancer cell in a mammal, preferably a human.

The present invention relates to a method inducing cell death comprising exposing a cell which overexpresses erbB2 to an effective amount of a succinate or malonate complex of formula 1 and said method further comprises exposing the cell to a growth inhibitory agent.

In another embodiment the present invention relates to a method inducing cell death comprising exposing a cell which overexpresses erbB2 to an effective amount of a monosuccinate, hemisuccinate, sesquisuccinate or di-malonate complex of formula 1 and said method further comprises exposing the cell to a growth inhibitory agent.

In one preferred embodiment the cell is exposed to a chemotherapeutic agent or radiation.

The invention further relates to a method of treating cancer in a human, wherein the cancer expresses the erbB2 receptor, comprising administering to the human a therapeutically effective amount of a succinate or malonate complex of formula 1. In a preferred embodiment the invention relates to a method of treating cancer in a human, wherein the cancer expresses the erbB2 receptor, comprising administering to the human a therapeutically effective amount of a monosuccinate, hemisuccinate, sesquisuccinate or di-malonate complex of formula 1. In one preferred embodiment of the present invention the cancer is not characterized by overexpression of erbB1 receptor. In another preferred embodiment the cancer is characterized by overexpression of the erbB1 and erbB2 receptor.

This invention also relates to a method for the treatment of a disorder associated with angiogenesis in a mammal, including a human, comprising administering to said mammal a succinate or malonate complex of formula 1, or solvate or prodrug thereof, that is effective in treating said disorder. In a preferred embodiment the invention relates a method for the treatment of a disorder associated with angiogenesis in a mammal, including a human, comprising administering to said mammal a monosuccinate, hemisuccinate, sesquisuccinate or di-malonate complex of formula 1, or solvate or prodrug thereof, that is effective in treating said disorder. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi*, *Yersinia* spp., *Bordetella pertussis*, and group A *Streptococcus*.

The terms "complex" or "complexes", as used herein, unless otherwise indicated, refers to an acid-base pair that has a defined stoichiometry and contains ionized, unionized and/or partially charged base and acid species, wherein the extent of proton transfer from acid (proton donor) to the base (proton acceptor) can vary in proportions from none, partial, to all. All complexes are termed with the suffix "ate" to represent a complex of a specific acid whose name ends in "ic". For example, a complex of a basic compound with succinic acid wherein the mole ratio of succinic acid to the basic compound is 1.5 is named as a "sesquisuccinate" of the basic compound. One of ordinary skill in the art will appreciate that the above definition of "complex" includes salt wherein the extent of proton transfer from acid to the base is substantially in full proportion (i.e., complete proton transfer).

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs; and (4) any tumors that proliferate by virtue of farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "a compound that has reduced affinity for the erbB1 receptor", as used herein, unless otherwise indicated, means wherein the compound is an erbB2 inhibitor and has a range of selectivities for erbB2 receptor over the erbB1 receptor between 50–1500, i.e., the compound is from 50 to 1500 times more selective for the erbB2 receptor over the erbB1 receptor. In a preferred embodiment the erbB2 inhibitor has a range of selectivities for erbB2 over erbB1 between 60–1200. In a more preferred embodiment the erbB2 inhibitor has a range of selectivities for erbB2 over erbB1 between 80–1000. In an even more preferred embodiment the erbB2 inhibitor has a range of selectivities for erbB2 over erbB1 between 90–500. In a most preferred embodiment the erbB2 inhibitor has a range of selectivities for erbB2 over erbB1 between 100–300. In the most preferred embodiment the erbB2 inhibitor has a range of selectivities for erbB2 over erbB1 between 110–200. The selectivity of the erbB2 inhibitor over the erbB1 inhibitor is measured using the whole cell (intact) assay described below.

DETAILED DESCRIPTION OF THE INVENTION

The present invention relates to succinate and malonate complexes of E-2-Methoxy-N-(3-{4-[3-methyl-4-(6-methyl-pyridin-3-yloxy)-phenylamino]-quinazolin-6-yl}-allyl)-acetamide.

In one preferred embodiment of the present invention relates to monosuccinate, hemisuccinate, sesquisuccinate and di-malonate complexe of E-2-Methoxy-N-(3-{4-[3-methyl-4-(6-methyl-pyridin-3-yloxy)-phenylamino]-quinazolin-6-yl}-allyl)-acetamide.

The invention further relates to a method making the monosuccinate, hemisuccinate, sesquisuccinate and di-malonate complexes of E-2-Methoxy-N-(3-{4-[3-methyl-4-(6-methyl-pyridin-3-yloxy)-phenylamino]-quinazolin-6-yl}-allyl)-acetamide.

The complexes of the present invention are useful in the treatment of hyperproliferative diseases, such as cancers, in mammals, especially humans, and to pharmaceutical compositions containing such compounds.

The complexes of the compound of formula I have been characterized using elemental analysis.

The in vitro activity of the compounds of formula 1 may be determined by the following procedure.

The in vitro activity of the compounds of formula 1 as erbB kinase inhibitors in intact cells may be determined by the following procedure. Cells, for example 3T3 cells transfected with human EGFR (Cohen et al. J. Virology 67:5303, 1993) or with chimeric EGFR/erbB2 kinase (EGFR extracellular/erbB2 intracellular, Fazioli et al. Mol. Cell. Biol. 11: 2040, 1991) are plated in 96-well plates at 12,000 cells per well in 100 µl medium (Dulbecco's Minimum Essential Medium (DMEM) with 5% fetal calf serum, 1% pen/streptomycin, 1% L-glutamine) and incubated at 37° C., 5% $CO_2$. Test compounds are solubilized in DMSO at a concentration of 10 mM, and tested at final concentrations of 0, 0.3 µM, 1 µM, 0.3 µM, 0.1 µM and 10 µM in the medium. The cells are incubated at 37° C. for 2 h. EGF (40 ng/ml final) is added to each well and cells incubate at room temperature for 15 min followed by aspiration of medium, then 100 µl/well cold fixative (50% ethanol/50% acetone containing 200 micromolar sodium orthovanadate) is added. The plate is incubated for 30 min at room temperature followed by washing with wash buffer (0.5% Tween 20 in phosphate buffered saline). Blocking buffer (3% bovine serum albumin, 0.05% Tween 20, 200 µM sodium orthovanadate in phosphate buffered saline, 100 µl/well) is added followed by incubation for 2 hours at room temperature followed by two washes with wash buffer. PY54 monoclonal anti-phosphotyrosine antibody directly conjugated to horseradish peroxidase (50 µl/well, 1 µg/ml in blocking buffer) or blocked conjugate (1 µg/ml with 1 mM phosphotyrosine in blocking buffer, to check specificity) is added and the plates incubated for 2 hours at room temperature. The plate wells are then washed 4 times with wash buffer. The colorimetric signal is developed by addition of TMB Microwell Peroxidase Substrate (Kirkegaard and Perry, Gaithersburg, Md.), 50 µl, per well, and stopped by the addition of 0.09 M sulfuric acid, 50 µl per well. Absorbance at 450 nM represents phosphotyrosine content of proteins. The increase in signal in EGF-treated cells over control (non-EGF treated) represents the activity of the EGFR or EGFR/chimera respectively. The potency of an inhibitor is determined by measurement of the concentration of compound needed to inhibit the increase in phosphotyrosine by 50% ($IC_{50}$) in each cell line. The selectivity of the compounds for erbB2 vs. EGFR is determined by comparison of the $IC_{50}$ for the EGFR transfectant vs. that for the erbB2/EGFR chimera transfectant. Thus, for example, a compound with an $IC_{50}$ of 100 nM for the EGFR transfectant and 10 nM for the erbB2/EGFR chimera transfectant is considered 10-fold selective for erbB2 kinase.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Where HPLC chromatography is referred to in the preparations and examples below, the general conditions used, unless otherwise indicated, are as follows. The column used is a ZORBAX™ RXC18 column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 mL/ minute.

In the following examples and preparations, "Et" means ethyl, "AC" means acetyl, "Me" means methyl, "ETOAC" or "ETOAc" means ethyl acetate, "THF" means tetrahydrofuran, and "Bu" means butyl.

EXAMPLE 1

Free Base of E-2-Methoxy-N-(3-{4-[3-methyl-4-(6-methyl-pyridin-3-yloxy)-phenylamino]-quinazolin-6-yl}-allyl)-acetamide The free base of E-2-Methoxy-N-(3-{4-[3-methyl-4-(6-methyl-pyridin-3-yloxy)-phenylamino]-quinazolin-6-yl}-allyl)-acetamide is prepared according to Example 182 (LMRS: 470.1, HPLC RT:5.05) using procedure G described in U.S. Ser. No. 09/883,752, filed Jun. 18, 2001, the disclosure of which is hereby incorporated herein by reference in its entirety. Procedure G from U.S. Ser. No. 09/883,752, is shown below:

Method G: Synthesis of E-N-(3-{4-[3-Chloro-4-(6-methyl-pyridin-3-yloxy)-phenylamino]-quinazolin-6-yl}-allyl)-acetamide (7):

E-(3-{4-[3-chloro-4-(6-methyl-pyridin-3-yloxy)-phenylamino]-quinazolin-6-yl}-allyl)-carbamic acid tert-butyl ester: To a solution of 7.53 mL of a 65% weight toluene solution of sodium bis(2-methoxyethoxy)aluminum hydride (Red-Al, 24.2 mmol) in 90 mL of tetrahydrofuran at 0° C. was added 5.0 g of (3-{4-[3-chloro-4-(6-methyl-pyridin-3-yloxy)-phenylamino]-quinazolin-6-yl}-prop-2-ynyl)-carbamic acid tert-butyl ester as a solid. The reaction was stirred at 0° C. for 2 hours, quenched with 10% aqueous potassium carbonate and extracted with ethyl acetate. The combined organics were dried and evaporated. The crude material was purified on 115 g of silica gel, eluting with 80% ethyl acetate/hexanes to afford 4.42 g of E-(3-{4-[3-chloro-4-(6-methyl-pyridin-3-yloxy)-phenylamino]-quinazolin-6-yl}-allyl)-carbamic acid tert-butyl ester. $^1$H NMR (CDCl$_3$): δ 8.66 (s, 1), 8.24 (m, 1), 8.03 (m, 2), 7.77–7.65 (m, 3), 7.13 (m, 2), 6.97 (d, J=8.7 Hz, 1), 6.54 (d, 1), 6.35 (m, 1), 4.90 (m, 1) 3.90 (m, 2), 2.52 (s, 3), 1.46 (s, 9).

E-[6-(3-amino-propenyl)-quinazolin-4-yl]-[3-chloro-4-(6-methyl-pyridin-3-yloxy)-phenyl]-amine. To a solution of 4.42 g of E-(3-{4-[3-chloro-4-(6-methyl-pyridin-3-yloxy)-phenylamino]-quinazolin-6-yl}-allyl)-carbamic acid tert-butyl ester in 21 mL of tetrahydrofuran was added 21 mL of 2 N hydrochloric acid. The mixture was heated at 60° C. for 3 hours, cooled to room temperature and basified with 10% aqueous potassium carbonate. Methylene chloride was added to the aqueous mixture and a solid precipitated. The solid was filtered and dried to yield 2.98 g of E-[6-(3-amino-propenyl)-quinazolin-4-yl]-[3-chloro-4-(6-methyl-pyridin-3-yloxy)-phenyl]-amine. $^1$H NMR (d$_6$ DMSO): δ 8.62 (s, 1), 8.53 (m, 1), 8.26 (m, 2), 7.99 (m, 1), 7.89 (m, 1), 7.77 (m, 1), 7.30 (m, 3), 6.67 (m, 2), 3.44 (m, 2), 2.47 (s, 3).

E-N-(3-{4-[3-Chloro-4-(6-methyl-pyridin-3-yloxy)-phenylamino]-quinazolin-6-yl}-allyl)-acetamide. A mixture of 14.4 μL (0.25 mmol) of acetic acid and 40.3 mg (0.33 mmol) of dicyclohexylcarbodiimide in 2 mL of methylene chloride were stirred for 10 minutes and treated with 100.3 mg of E-[6-(3-amino-propenyl)-quinazolin-4-yl]-[3-chloro-4-(6-methyl-pyridin-3-yloxy)-phenyl]-amine. The reaction was allowed to stir at room temperature overnight. The precipitate which formed was filtered and chromatographed on silica gel, eluting with 6–10% methanol/chloroform to afford 106 mg of the title compound; mp 254–256° C.; $^1$H NMR (d$_6$ DMSO): δ 9.88 (s, 1), 8.58 (s, 1), 8.48 (m, 1), 8.20 (m, 3), 7.95 (m, 1), 7.83 (m, 1), 7.71 (d, J=8.7 Hz, 1), 7.24 (m, 2), 7.19 (d, J=8.7 Hz, 1), 6.61 (d, J=16.2 Hz, 1), 6.48 (m, 1), 3.90 (m, 2).

EXAMPLE 2

Sesquisuccinate Complex of E-2-Methoxy-N-(3-{4-[3-methyl-4-(6-methyl-pyridin-3-yloxy)-phenylamino]-quinazolin-6-yl}-allyl)-acetamide To a solution of E-2-Methoxy-N-(3-{4-[3-methyl-4-(6-methyl-pyridin-3-yloxy)-phenylamino]-quinazolin-6-yl}-allyl)-acetamide in hot THF/acetone (5/100) two equivalents of succinic acid were added. Crystals slowly formed as the solution cooled. After slurrying overnight, the crystals were filtered and rinsed with acetone. The product was isolated as a white solid and verified as the sesquisuccinate complex of E-2-Methoxy-N-(3-{4-[3-methyl-4-(6-methyl-pyridin-3-yloxy)-phenylamino]-quinazolin-6-yl}-allyl)-acetamide by CHN analysis. Calculated: C=61.29, H=5.61, N=10.83, Experimental: C=61.04, H=5.61, N=10.85.

EXAMPLE 3

Monosuccinate Complex of E-2-Methoxy-N-(3-{4-[3-methyl-4-(6-methyl-pyridin-3-yloxy)-phenylamino]-quinazolin-6-yl}-allyl)-acetamide The monosuccinate complex of E-2-Methoxy-N-(3-{4-[3-methyl-4-(6-methyl-pyridin-3-yloxy)-phenylamino]-quinazolin-6-yl}-allyl)-acetamide can be prepared by methods well known to those of ordinary skill in the art, for example, using the process described in Example 2 herein by varying the amount of succinic acid.

EXAMPLE 4

Hemisuccinate Complex of E-2-Methoxy-N-(3-{4-[3-methyl-4-(6-methyl-pyridin-3-yloxy)-phenylamino]-quinazolin-6-yl}-allyl)-acetamide The hemisuccinate complex of E-2-Methoxy-N-(3-{4-[3-methyl-4-(6-methyl-pyridin-3-yloxy)-phenylamino]-quinazolin-6-yl}-allyl)-acetamide can be prepared by methods well known to those of ordinary skill in the art, for example, using the process described in Example 2 herein by varying the amount of succinic acid.

EXAMPLE 5

Di-malonate Complex of E-2-Methoxy-N-(3-{4-[3-methyl-4-(6-methyl-pyridin-3-yloxy)-phenylamino]-quinazolin-6-yl}-allyl)-acetamide To a solution of E-2-Methoxy-N-(3-{4-[3-methyl-4-(6-methyl-pyridin-3-yloxy)-phenylamino]-quinazolin-6-yl}-allyl)-acetamide (1 g) in hot acetone (100 ml) was added two equivalents of malonic acid (443 mg). As the solution cooled crystals formed after 2 hours, the crystals were filtered after slurrying overnight and rinsed with acetone. The light yellow solid (1.36 g, 94%) was confirmed as the di-malonate complex of E-2-Methoxy-N-(3-{4-[3-methyl-4-(6-methyl-pyridin-3-yloxy)-phenylamino]-quinazolin-6-yl}-allyl)-acetamide by CHN analysis. Calculated: C=58.49, H=5.21, N=10.33, Experimental: C=58.30, H=5.12, N=10.33

What is claimed is:

1. A succinate complex of E-2-Methoxy-N-(3-{4-[3-methyl-4-(6-methyl-pyridin-3-yloxy)-phenylamino]-quinazolin-6-yl}-allyl)-acetamide.

2. The compound of claim 1, wherein the succinate complex is a monosuccinate or sesquisuccinate complex of E-2-Methoxy-N-(3-{4-[3-methyl-4-(6-methyl-pyridin-3-yloxy)-phenylamino]-quinazolin-6-yl}-allyl)-acetamide.

3. The compound of claim 2, wherein the succinate complex is a monosuccinate complex of E-2-Methoxy-N-(3-{4-[3-methyl-4-(6-methyl-pyridin-3-yloxy)-phenylamino]-quinazolin-6-yl}-allyl)-acetamide.

4. The compound of claim 2, wherein the succinate complex is a hemisuccinate complex of E-2-Methoxy-N-(3-{4-[3-methyl-4-(6-methyl-pyridin-3-yloxy)-phenylamino]-quinazolin-6-yl}-allyl)-acetamide.

5. The compound of claim 2, wherein the succinate complex is a sesquisuccinate complex of E-2-Methoxy-N-(3-{4-[3-methyl-4-(6-methyl-pyridin-3-yloxy)-phenylamino]-quinazolin-6-yl}-allyl)-acetamide.

6. The compound of claim 1, wherein the malonate complex is a di-malonate complex of E-2-Methoxy-N-(3-{4-[3-methyl-4-(6-methyl-pyridin-3-yloxy)-phenylamino]-quinazolin-6-yl}-allyl)-acetamide.

7. A pharmaceutical composition comprising an amount of a compound according to claim 1 effective to treat a hyperproliferative disorder in a mammal, and a pharmaceutically acceptable carrier, wherein said hyperproliferative disorder is selected from the group consisting of breast cancer and ovarian cancer.

8. The pharmaceutical composition of claim 7, wherein the composition is adapted for oral administration.

9. The pharmaceutical composition of claim 8, wherein the pharmaceutical composition is in tablet form.

10. The pharmaceutical composition of claim 8, wherein the pharmaceutical composition is in capsule form.

11. A method of treating cancer in a mammal comprising administering to said mammal an amount of a monosuccinate or sesquisuccinate complex of E-2-Methoxy-N-(3-{4-[3-methyl-4-(6-methyl-pyridin-3-yloxy)-phenylamino]-quinazolin-6-yl}-allyl)-acetamide that is effective in treating cancer, wherein said cancer is selected from the group consisting of breast cancer and ovarian cancer.

12. The method according to claim 11, wherein said cancer is breast cancer.

13. The method according to claim 11, wherein said cancer is ovarian cancer.

14. A method for the treatment of cancer in a mammal which comprises administering to said mammal an amount of a compound of claim 1 that is effective in treating cancer in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens, wherein said cancer is selected from the group consisting of breast cancer and ovarian cancer.

15. The method of claim 14, which comprises administering to said mammal an amount of a compound of claim 1 that is effective in treating cancer in combination with a cytotoxic.

16. The method of claim 15, which comprises administering to said mammal an amount of a compound of claim 1 that is effective in treating cancer in combination with Taxol®.

17. A method for the treatment of cancer in a mammal which comprises administering to said mammal an amount of the compound of claim 1 that is effective in treating cancer in combination with a compound selected from the group consisting of Cyclophosphamide, 5-Fluorouracil, Floxuridine, Gemcitabine, Vinblastine, Vincristine, Daunorubicin, Doxorubicin, Epirubicin, Tamoxifen, Methylprednisolone, Cisplatin, Carboplatin, CPT-11, gemcitabine, paclitaxel, and docetaxel.

18. The method of claim 17, comprises administering to said mammal an amount of a compound of claim 1 that is effective in treating cancer in combination with a compound selected from the group consisting Tamoxifen, Cisplatin, Carboplatin, paclitaxel and docetaxel.

19. A method for treating a mammal having a disease characterized by an overexpression of erbB2, comprising administering to the mammal the compound of claim 1 in an amount that is effective in treating a disease characterized by the overexpression of erbB2, where said disease is selected from the group consisting of breast cancer and ovarian cancer.

20. A method for treating a mammal having cancer characterized by an overexpression of erbB2, comprising administering to the mammal the compound of claim 2 in an amount that is effective in treating said cancer characterized by the overexpession of erbB2, where said cancer is selected from the group consisting of breast cancer and ovarian cancer.

21. A method for inducing cell death comprising exposing a cell which overexpresses erbB2 to an effective amount of the compound of claim 1, wherein said cell is selected from the group consisting of a breast cancer cell and an ovarian cancer cell.

22. The method of claim 21, wherein the cell is in a mammal.

23. The method of claim 21, wherein the mammal is a human.

24. The method of claim 21, further comprising exposing the cell to growth inhibitory agent.

25. The method of claim 21, further comprising exposing the cell to a chemotherapeutic agent.

26. The method of claim 21, further comprising exposing the cell to radiation.

27. A method of treating cancer in a human, wherein the cancer expresses the erbB2 receptor and said cancer is selected from the group consisting of breast cancer and ovarian cancer, comprising administering to the human a therapeutically effective amount of the compound of claim 1 that has reduced affinity for the erbB1 receptor.

28. The method of claim 27, wherein the cancer is not characterized by overexpression of erbB1 receptor.

29. The method of claim 27, wherein the cancer is characterized by overexpression of the erbB1 and erbB2 receptor.

30. A method of treating cancer in a mammal comprising administering to said mammal an amount of a di-malonate complex of E-2-Methoxy-N-(3-{4-[3-methyl-4-(6-methyl-pyridin-3-yloxy)-phenylamino]-quinazolin-6-yl}-allyl)-acetamide that is effective in treating cancer, wherein said cancer is selected from the group consisting of breast cancer and ovarian cancer.

* * * * *